United States Patent [19]

Barberet et al.

[11] Patent Number: Plant 6,289

[45] Date of Patent: Sep. 13, 1988

[54] CARNATION PLANT NAMED 'LONZIATA'

[75] Inventors: Nicole Barberet; Yves Ducloux, both of Antibes, France

[73] Assignee: Laboratoire de Physiologie Vegetale de la Londe, La Londe, France

[21] Appl. No.: 890,724

[22] Filed: Jul. 25, 1986

[51] Int. Cl.[4] ..... A01H 5/00

[52] U.S. Cl. ..... Plt./71

[58] Field of Search ..... Plt./70, 71

*Primary Examiner*—Robert E. Bagwill

*Attorney, Agent, or Firm*—Charles W. Rummler

EXEMPLARY CLAIM

A new variety of spray carnation having relatively small, bright red blooms of a crimson and rose red coloration which are produced profusely, during intermittent spring, midseason and fall blooming periods, in a spray formation carried on long, strong stems averaging a height of about 115 centimeters at eight months, with flower stems averaging about 69 centimeters in length and the plant having a vigorous, upright and rather rigid growth habit with an abundant production of foliage.

1 Drawing Sheet

BACKGROUND OF THE NEW PLANT

This new carnation variety originated as a seedling resulting from our crossing of selected varieties from among our collection of carnation plants maintained at La Londe, Les Maures, France, for breeding purposes, the crossing from which this seedling resulted being done by us at La Londe with the object of producing a spray plant having nice color, good quality and a strong resistance to *Fusarium oxysporum.* This particular seedling was selected for propagation and test because of its tall, sturdy growth habit and its profuse production of pleasingly red flowers and our progressive propagation of this new plant, by cuttings, at La Londe clearly demonstrated that the novel characteristics that we had noted in the parent seedling would hold true from generation to generation and appeared to be firmly fixed.

DESCRIPTION OF THE DRAWING

Our new variety of spray carnation is illustrated by the accompanying photographic drawing which shows, in full color, the upper portion of a typical spray stem bearing buds and blossoms in various stages from tight new buds to fully opened flowers, the colors shown being as nearly true as it is reasonably possible to obtain by conventional photographic procedures.

DESCRIPTION OF THE NEW PLANT

The following is a detailed description of our new carnation plant based upon observation of greenhouse grown plants made at La Londe and at Antibes, France, early in 1986, the color designations being according to the R.H.S. Colour Chart published by The Royal Horticultural Society of London, England.

THE PLANT

Origin: Seedling

Parentage:

*Seed parent.*—Stock Variety No. 76 MC 6.

*Pollen parent.*—Stock Variety No. 79 MFG 2. These stock varieties were selected from carnations growing among our collection maintained at La Londe, Les Maures, France, for breeding purposes, the selected varieties being identified in our breeding records maintained in our office at La Londe.

Classification:

*Botanic.*—*Dianthus caryphyllus.*

*Commercial.*—Spray carnation.

Form: Tall, erect bush having at least four stems emitted near the ground from the main stem.

Height: About 115 cm. at eight months.

Main stem:

*Length.*—Less than 15 cm. due to pinching.

Branching character: Fairly numerous and alternate.

Growth habit: Vigorous, upright and rigid.

Foliage:

*Quantity.*—Abundant.

*Number of leaves.*—More than 120.

*Size of leaf.*—Averages about 8.7 cm. long and 0.8 cm. wide, at the seventh node.

*Shape.*—Linear with acute apex and curved margins.

*Texture.*—Leathery.

*Color.*—Upper side — 189B. Under side — 189B.

*Leaflets.*—None.

*Ribs, veins and rachis.*—Hardly noticeable.

THE BUD

Size: Small.

*Diameter.*—About 1.1 cm., in average.

*Length.*—About 2.4 cm., in average.

Form: Generally ovate.

Rate of opening: Normal for carnations.

Color:

*When sepals first divide and petals begin to unfurl-*.—The colors are the same as at full bloom.

Sepals:

*Number.*—5 to 7.

*Shape.*—Joined at the lower part with the upper portion generally ovate with mucronate tip. The sepals are hooded over the bud before dividing and when the flowers open, the sepals stand up and curl back.

*Color.*—143A and 144C.

*Striae.*—Longitudinal.

Calyx:

*Size.*—Medium.

*Shape.*—Long cylindrical.

*Splitting.*—The calyx does not split.

*Aspect.*—Smooth.

Flower stem:

*Length.*—About 69 cm., in average.
*Character.*—Erect and rather rigid.
*Color.*—189B.

THE FLOWER

Blooming habit: Recurrent, blooming profusely during spring, midseason and fall periods with a tendency to give fewer blooms in the fall.
Size of bloom: Small.
*Diameter.*—About 4.5 cm., in average.
*Depth.*—About 2.2 cm., in average.
Borne: In a cluster.
Shape:
*When bloom first opens.*—High centered.
*When bloom matures.*—Dome shaped.
Petalage:
*Number of petals.*—41, in average.
*Arrangement.*—Imbricated.
*Form.*—Generally fan shaped with deeply serrated end magin.
*Texture.*—Leathery.
*Appearance.*—Shiny.
*Color.*—Both outer and inner petals: Upper side: Body — 52A and 58B with the lighter color at the outer margins. Base — Whitish. Reverse side — 52B.
Petaloids:
*Number.*—Less than ten.
*Size.*—Smaller than petals.
*Color.*—The same as the petals.
Flower stem:
*Length.*—About 69 cm., cut at the tenth node.
*Color.*—189A.

*Character.*—Sturdy and upright.
Persistence: The flowers hang on and dry.
Fragrance: Strong.
Disease resistance: Very resistant to *Fusarium oxysporum* as observed I.N.R.A. Antibes, france.
Lasting quality:
*As a cut flower.*—At least 10 days in vase keeping.

REPRODUCTIVE ORGANS

Stamens:
*Number.*—0 to b 15.
*Arrangement.*—Around the ovary when present.
*Anthers.*—Size: About 4 mm. long. Color: Whitish.
*Filaments.*—Length: About 2.5 cm., in average. Color: Whitish.
Pistils:
*Number.*—Two.
*Styles.*—Length: About 1.6 cm. Color: Whitish.
*Stigmas.*—Color: Whitish and pink at the extremity.
Character of ovary: Ribbed.

This new carnation variety most nearly resembles 'Londeton' U.S. Plant Pat. No. 5,511) but differs from 'Londeton' by having a more abundant vegetation and being very resistant to *Fusarium oxysporum.*

We claim:

1. A new and distinct variety of spray carnation, substantially as herein shown and described, characterized by its profuse but intermittent flower production, its tall, vigorous and upright growth habit, reaching a height of about 115 centimeters at eight months with flower stems averaging about 69 centimeters in length.

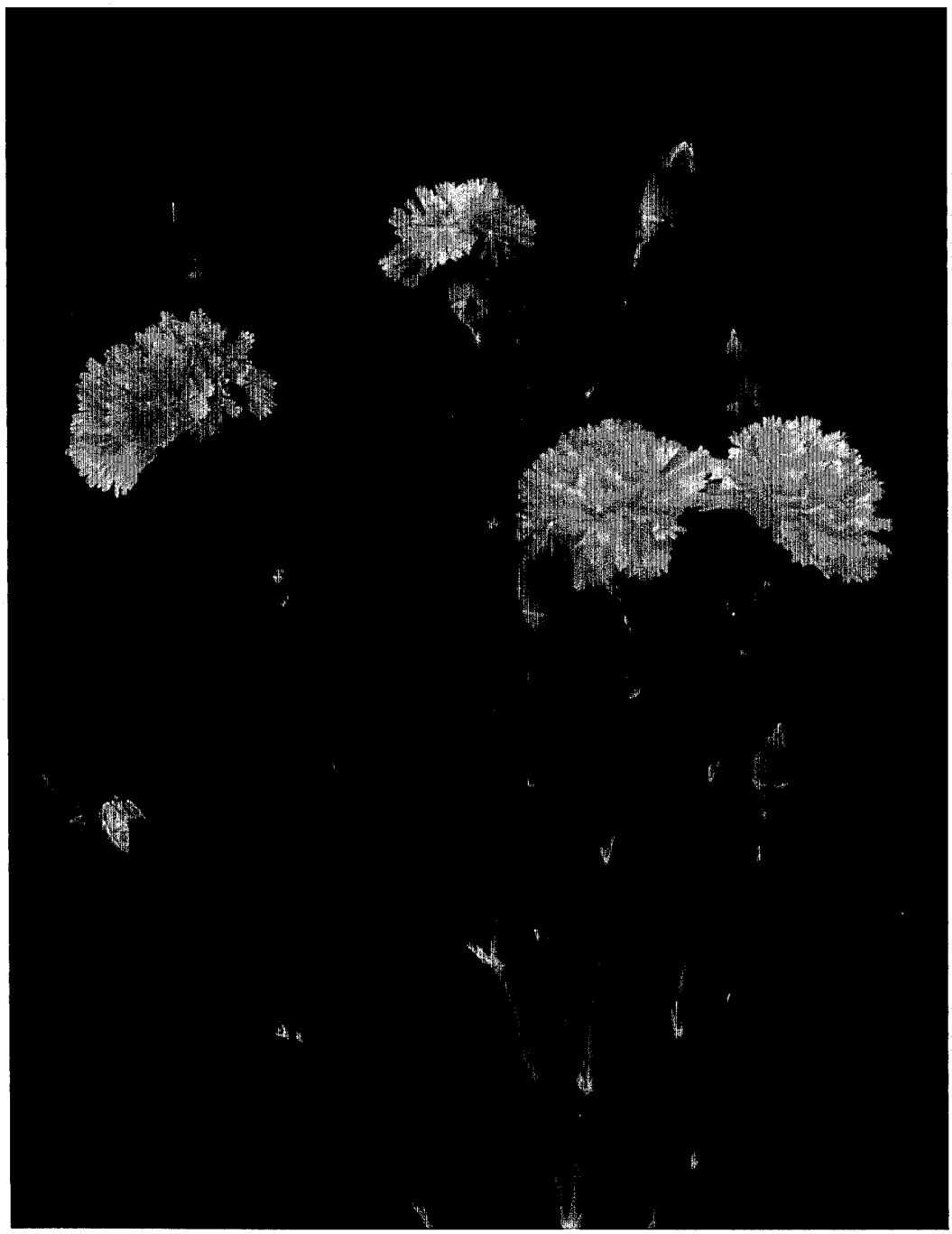

* * * * *